United States Patent [19]

Landgraf

[11] Patent Number: 5,655,907
[45] Date of Patent: Aug. 12, 1997

[54] ROTATABLE TOOL SUITABLE FOR HIGH SPEED DRIVE

[75] Inventor: Hermann Landgraf, Lorsch, Germany

[73] Assignee: Siemens Aktiengesellschaft, Munich, Germany

[21] Appl. No.: 552,436

[22] Filed: Nov. 3, 1995

Related U.S. Application Data

[63] Continuation of Ser. No. 196,466, Feb. 15, 1994, abandoned.

[30] Foreign Application Priority Data

Feb. 15, 1993 [DE] Germany .................. 43 04 515.4

[51] Int. Cl.⁶ .................................................. A61C 3/02
[52] U.S. Cl. ................................................... 433/165
[58] Field of Search ................... 433/165, 166, 433/84

[56] References Cited

U.S. PATENT DOCUMENTS

| | | | |
|---|---|---|---|
| 2,442,033 | 5/1948 | Brantly et al. | 433/165 |
| 3,842,632 | 10/1974 | Nelson | 433/165 |
| 3,892,117 | 7/1975 | Nelson | 433/165 |
| 4,975,056 | 12/1990 | Eibofner | 433/165 |
| 5,100,322 | 3/1992 | Weissman | 433/166 |
| 5,261,818 | 11/1993 | Shaw | 433/165 |

FOREIGN PATENT DOCUMENTS

| | | |
|---|---|---|
| 0 455 452 | 11/1991 | European Pat. Off. . |
| 500 485 | 6/1930 | Germany . |
| 661856 | 6/1938 | Germany .................. 433/165 |
| 1 294 592 | 5/1969 | Germany . |
| 267 692 | 5/1989 | Germany . |
| 38 08 707 | 10/1989 | Germany . |
| 617771 | 2/1949 | United Kingdom .......... 433/166 |
| 732124 | 6/1955 | United Kingdom .......... 433/165 |
| WO89/08534 | 9/1989 | WIPO . |

OTHER PUBLICATIONS

*Technica*, 20/1980, p. 1762.

Primary Examiner—Cary E. O'Connor
Attorney, Agent, or Firm—Hill, Steadman & Simpson

[57] ABSTRACT

A rotatable tool that is suitable for high-speed drives has a shaft for holding the tool in a suitable chucking device and one end of the shaft contains a tool head with an active working surface. To provide improved cooling of the tool, the tool head is provided with a central in-flow channel fashioned as a blind hole from which a plurality out-flow channels discharge to the working surface of the tool head.

10 Claims, 3 Drawing Sheets

ROTATABLE TOOL SUITABLE FOR HIGH SPEED DRIVE

This is a continuation of application Ser. No. 08/196,466, filed Feb. 15, 1994, now abandoned.

BACKGROUND OF THE INVENTION

The present invention is directed to a tool that can be placed into rotation, and is suitable for high-speed drive. The tool is capable of having a coolant externally supplied to it and comprises a shaft for holding the tool in a suitable chucking mechanism of the drive at one end of the shaft and comprises a tool head with an active work surface at the other end of the shaft.

Tools which are required to have a relatively great chip-removing power and which operate at extremely high speeds must be adequately cooled. To this end, it is standard to conduct a suitable coolant, usually water or what is referred to as "drill water", onto the tool and to, thus, cool the surfaces to be processed and the working surfaces of the tool as well.

East German Patent DD-267 692 A1 discloses a cutter of a rotating, chip-removing tool that has a comparatively large diameter, for example a knife head for a milling machine. This tool is cooled in that the coolant is sprayed into an annular space in an intentional fashion proceeding from a back side of the tool. Radially extending webs are located in the annular space, and these webs respectively project into the annular space behind the admission opening of the delivery channel as viewed in the rotational sense of the tool. Further conveying of the coolant occurs via a plurality of channels proceeding from the annular space, and these channels proceed from the shaft obliquely outward to the cutters placed at the periphery. The feed point, thus, has a smaller diameter than the exit location at the blades. An increased pressure that drives the coolant outward occurs due to the cross sectional constrictions and also is promoted by the centrifugal force upon rotation of the tool. This type of coolant guidance is relatively complicated, is only suitable for tools having a larger diameter and, due to the design, is suitable for only one rotational sense.

Technica 20/1980, p. 1762, discloses a drill having a cooling channel to continuously cool the main cutters of the drill. The cooling liquid is conducted under pressure into the cutter region proceeding from the tool shaft. The feed of the cooling liquid occurs either by a delivery ring arranged at a shaft end, and this conducts the cooling liquid into the inner cooling channel of the drill and, thus, directly into the cutter region, or the shaft may be provided with a central feed channel and lateral channels departing therefrom via which the cooling fluid is conducted into the cutting region. Here, too, the coolant is conducted via inwardly disposed channels.

In the dental field, tools are employed which have externally applied coolant for drilling, milling, grinding and polishing. These tools are operated in a speed range of up to 30,000 rpm. A water/air mixture is usually supplied for cooling the tool and the preparation area as well. However, this water/air mixture forms a fine fog around the tool tip as a consequence of the turbulence caused by the tool.

Adequate cooling is not assured in tools of the traditional type, particularly given the great stress on the tool as a result wherein premature wear of the tool and/or an inadmissible overheating of the material to be processed can occur.

SUMMARY OF THE INVENTION

The present invention is directed to providing improved cooling for a tool which would alleviate the above-mentioned problems. To accomplish this goal, the present invention is directed to an improvement for a rotary tool for a high-speed drive, which tool can be supplied with a cooling agent from the outside, said tool having a shaft with one end being constructed for engagement in a chucking device of the drive, said shaft having a second end with a tool head with an active surface. The improvements are that the tool head is provided with an axial blind bore extending inward from an end of the tool head to form an axial in-flow channel, said head having a plurality of out-flow channels extending from the in-flow channel and discharging at the working surface.

The invention is based on the perception that a pressure and eddy or wake region that causes a pump effect is formed in the work area at high speeds, such as given a high speed rotation of the tool. At high speeds, the air flow is produced and will suck or draw the supplied coolant in the centrally placed in-flow channel of the tool and, in turn, allows it to flow off via the radially or obliquely outwardly proceeding out-flow channels. An extremely good cooling of the tool from the inside will, thus, occur. In addition, the working surface, such as the cutters of the tool, are cooled by the coolant emerging from the out-flow channels in the region of the working surfaces. The cooling effect is, thereby, all the more effective when the tool operates at higher speeds.

Other advantages and features of the invention will be readily apparent from the following description of the preferred embodiments, the drawings and claims.

DESCRIPTION OF THE PREFERRED EMBODIMENTS

Figure 1:
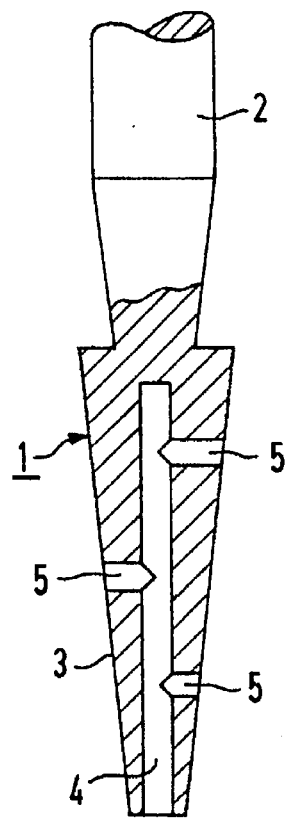
FIG. 1 is a cross sectional view of a tool head of a tool in accordance with the present invention.

The principles of the present invention are particularly useful when incorporated in a tool, generally indicated at 1, which tool is particularly suitable for employment in a dental instrument. The tool 1 has a cylindrical shaft 2, which is constructed to be introduced in a known way in a suitable chucking mechanism of the drive of the dental instrument. Lying opposite the shaft 2, the tool 1 has a conical tool head 3 that, in turn, comprises a central in-flow channel 4 constructed as a blind hole from the end of the head 3. A plurality of out-flow channels 5 lead radially outward from the channel 4 toward the exterior working surface. As may be seen from the illustration, the out-flow channels 5 lie in a plurality of planes and proceed transversely relative to the longitudinal axis of the tool and are arranged on the circumference so that no unbalanced state will occur during rotation of the tool. Advantageously, three out-flow channels are provided at the circumference or working surface of the head 3.

Figure 2:
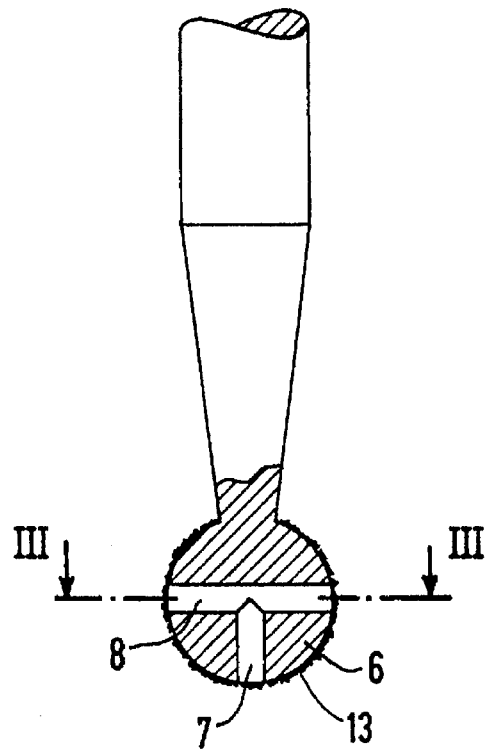
FIG. 2 is a cross sectional view of a tool head in accordance with embodiment of the present invention.

A second embodiment of the tool is illustrated in FIG. 2 and comprises a spherical tool head 6 which has a central in-flow channel 7. The channel 7 is connected to a through out-flow channel 8, which is approximately centrally placed on a spherical head and proceeds transversely therethrough.

Figure 5:
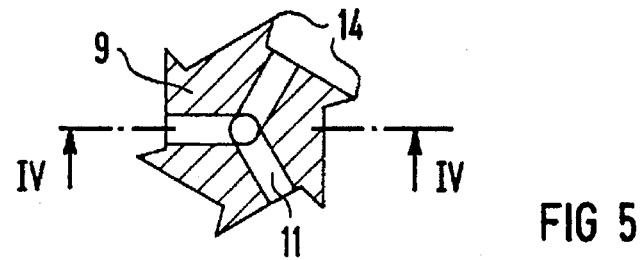
FIG. 5 is a cross sectional view taken along the lines V—V of FIG. 4.
Figure 4:
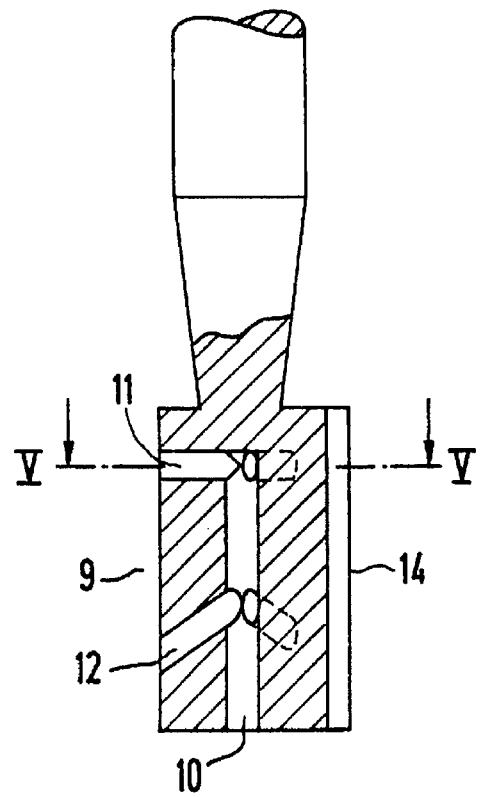
FIG. 4 is a cross sectional view taken along the lines IV—IV of FIG. 5 of an embodiment of a tool head in accordance with the present invention.

Another embodiment is illustrated in FIGS. 4 and 5 and has a tool head 9 which is a cylindrical tool head that likewise comprises a centrally-placed in-flow channel 10 extending from a lower end of the head 9. The in-flow channel 10 is connected, first, to three out-flow channels 11 arranged in the upper part of the tool head and also to three out-flow channels 12 that proceed at arbitrary angles relative to the tool axis. As illustrated, these channels 12 proceed obliquely in a downward direction. The out-flow channels 11 and 12 are arranged so that no unbalanced state occurs during rotation. As illustrated in FIG. 5, there are three channels 11 which extend symmetrically around the head so that each channel is separated by an angle of 120°.

Figure 6:
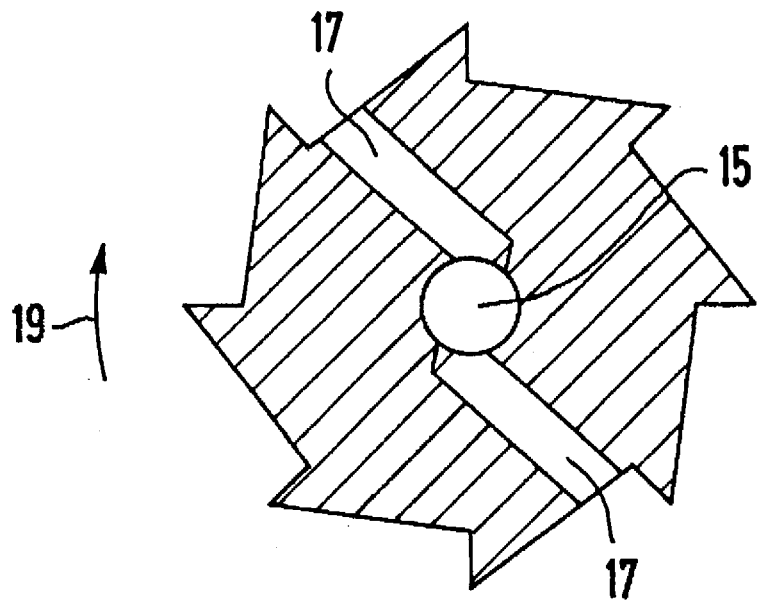
FIG. 6 is a cross sectional view similar to FIG. 5 of a modification of the embodiment illustrated in FIG. 5.
Figure 7:
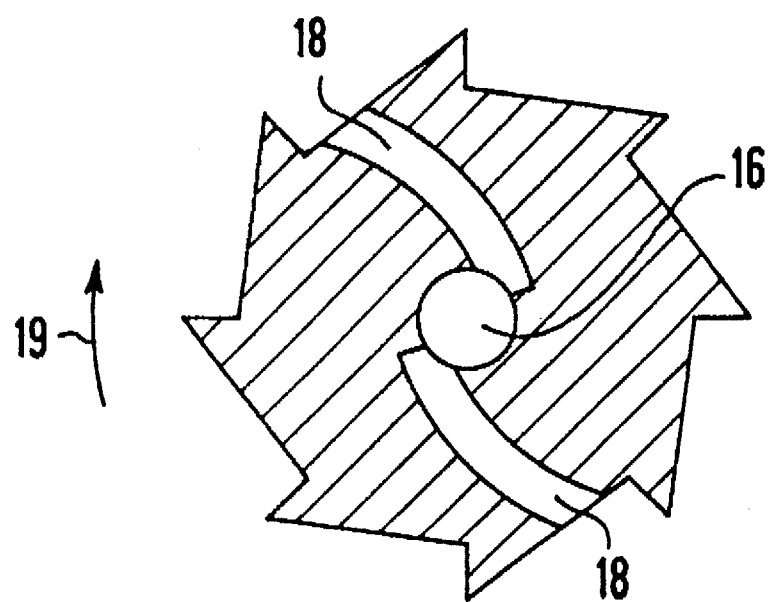
FIG. 7 is a cross sectional view similar to that of FIG. 5 of yet another modification.

Additional embodiments of a tool of the invention which are provided with cutters, such as the tool of FIGS. 4 and 5, are shown in FIGS. 6 and 7. In FIG. 6, a central in-flow channel 15 is provided with out-flow channels 17, while in FIG. 7, a central in-flow channel 16 is provided with out-flow channels 18. The characterizing feature of these embodiments are that the out-flow channels, such as 17 and 18, do not centrally depart from the in-flow channels 15 and 16, but tangentially depart. In addition, the channels 18 are constructed to extend along a curved path with the curvature being arranged and directed opposite the direction of the rotational sense of the tool, which is indicated by arrows 19. An even better out-flow of the coolant and, thus, a more efficient spray effect is achieved with the arrangement of FIG. 7 over that present in the arrangement of FIG. 6.

Figure 3:
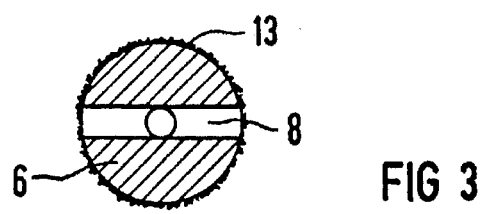
FIG. 3 is a cross sectional view taken along the lines III—III of FIG. 2.

The exemplary embodiments only represent a selection from possibilities for providing tool heads with a more effective inside cooling in combination with a cooling of the outer working surfaces. The advantages are established for both tools which have a diamond coating working surface indicated at 13 in FIGS. 2 and 3, as well as in tools that are provided with cutters, such as cutters 14 for the tools of FIGS. 4 and 5, as well as similar cutters in the tools illustrated in FIGS. 6 and 7.

Although the advantages that have been presented are especially established given use of the tool in the dental field, wherein the tools are utilized with gentle drill drives, the employment is not limited to this field. The employment of this tool can be advantageously utilized in other fields. Thus, for example, the cooling of the invention can be utilized in any tool that is employed in a machine tool manufacture, for example one using high-speed spindles.

Although various minor modifications may be suggested by those versed in the art, it should be understood that I wish to embody within the scope of the patent granted hereon all such modifications as reasonably and properly come within the scope of my contribution to the art.

I claim:

1. In a rotatable tool for high-speed drive, which tool can be supplied with a cooling agent from the outside, said tool having a shaft with one end being constructed for engagement in a chucking device of the drive, said shaft having a second end with a tool head with an active working surface, the improvements comprising the tool head being provided with an axial blind bore extending inward from an end of the head to form an axial in-flow channel, said head having a plurality of out-flow channels extending from the in-flow channel and discharging at the working surface, wherein the out-flow channels extend tangentially from the in-flow channel, wherein the out-flow channels are arranged along a curved path extending opposite the rotational sense of the tool.

2. A rotatable dental tool for a high-speed dental drive, which tool can be supplied with a cooling agent from the outside,
said rotatable dental tool consisting of a one-piece shaft with a first end being constructed for engagement in a chucking device of the high-speed dental drive,
said one-piece shaft having a second end with a tool head with a distal end and a working surface on a radial surface thereof,
said tool head having means for drawing a cooling agent from the outside at the distal end of the tool head and discharging the cooling agent directly on the working surface of the tool head,
said means consisting of an axial blind bore and a plurality of out-flow channels, said axial blind bore extending on a center of the rotational axis of said one-piece shaft inward from said second end of said tool head to form an axial in-flow channel for drawing the cooling agent from outside of said tool head into said tool head along said rotational axis, said axial blind bore being free of any obstructions, said plurality of out-flow channels being bores extending tangentially from a surface of the axial blind bore.

3. A rotatable dental tool according to claim 2, wherein the plurality of out-flow channels proceed transversely relative to the longitudinal axis of the shaft and are provided at the circumference of the tool head.

4. A rotatable dental tool according to claim 3, wherein the out-flow channels are arranged and distributed on a plurality of planes that proceed transversely relative to the longitudinal axis of the shaft.

5. A rotatable dental tool according to claim 4, wherein at least some of the outflow channels are arranged at an angle relative to the tool axis that deviates from 90°.

6. A rotatable dental tool according to claim 4, wherein the out-flow channels are arranged with a curvature opposite the rotational sense of the tool.

7. A rotatable dental tool according to claim 4, wherein the tool is a drilling, milling and grinding tool.

8. A rotatable dental tool according to claim 2, wherein at least some of the out-flow channels are arranged at an angle relative to the tool axis that deviates from 90°.

9. A rotatable dental tool for high-speed dental drive, said rotatable dental tool consisting of a one-piece shaft with a first end being constructed for engagement in a chucking device of the high-speed dental drive, said shaft having a second end with a tool head with an active outer working surface thereon and a distal end, the tool head having means for drawing a cooling agent from the outside at the distal end of the tool head and discharging the cooling agent directly on the active outer working surface, said means consisting of an axial blind bore extending inward from the distal end on the center of the axis of the shaft to form an axial in-flow channel and a plurality of out-flow channels extending from the in-flow channel and discharging at the outer working surface, said axial blind bore being free of any obstructions, and said out-flow channels being bores of a constant diameter extending tangentially from a surface of the axial blind bore.

10. A rotatable dental tool according to claim 8, wherein the bores of the out-flow channel extend on a curved path.

* * * * *